(12) United States Patent
Jeong et al.

(10) Patent No.: US 9,783,489 B2
(45) Date of Patent: Oct. 10, 2017

(54) PSEUDO CERAMIDE COMPOUND, AND PHARMACEUTICAL COMPOSITION AND COSMETIC COMPOSITION COMPRISING SAME

(71) Applicant: NEOPHARM CO., LTD., Daejeon (KR)

(72) Inventors: Se Kyoo Jeong, Daejeon (KR); Bong Woo Kim, Daejeon (KR); Bu Mahn Park, Daejeon (KR); Jeong Eun Jeon, Daejeon (KR); Byung Gee Kim, Seoul (KR)

(73) Assignee: NEOPHARM CO., LTD., Daejeon (KR)

( * ) Notice: Subject to any disclaimer, the term of this patent is extended or adjusted under 35 U.S.C. 154(b) by 0 days.

(21) Appl. No.: 15/106,777

(22) PCT Filed: Dec. 23, 2014

(86) PCT No.: PCT/KR2014/012726
§ 371 (c)(1),
(2) Date: Jun. 20, 2016

(87) PCT Pub. No.: WO2016/105290
PCT Pub. Date: Jul. 16, 2015

(65) Prior Publication Data
US 2017/0036995 A1    Feb. 9, 2017

(30) Foreign Application Priority Data

Jan. 13, 2014 (KR) ........................ 10-2014-0004029

(51) Int. Cl.
*C07C 235/80* (2006.01)
*A61K 8/68* (2006.01)
*A61K 31/16* (2006.01)
*A61Q 19/00* (2006.01)

(52) U.S. Cl.
CPC .............. *C07C 235/80* (2013.01); *A61K 8/68* (2013.01); *A61K 31/16* (2013.01); *A61Q 19/00* (2013.01); *A61Q 19/007* (2013.01)

(58) Field of Classification Search
CPC combination set(s) only.
See application file for complete search history.

(56) References Cited

U.S. PATENT DOCUMENTS

| 6,221,371 B1 | 4/2001 | Baik et al. |
| 7,344,868 B2 | 3/2008 | Lassalle et al. |
| 2010/0173995 A1 | 7/2010 | Park et al. |
| 2010/0286102 A1 | 11/2010 | Vielhaber |

FOREIGN PATENT DOCUMENTS

| KR | 1020000052640 A | 8/2000 |
| KR | 1020010019411 A | 3/2001 |
| KR | 100570553 B1 | 4/2006 |
| KR | 100693292 B1 | 3/2007 |
| KR | 1020100001374 A | 1/2010 |

OTHER PUBLICATIONS

Arana et al. "Ceramide and ceramide 1-phosphate in health and disease" Lipids in Health and Disease 2010, 9, 2-12.*
Chemical Abstract Service STN Registry Nos. 1597432-40-0 [entered STN: May 5, 2014].*
Chemical Abstract Service STN Registry No. 1597432-39-7 [entered STN: May 5, 2014].*
ISA Korean Intellectual Property Office, International Search Report Issued in Application No. PCT/KR2014/012726, Apr. 1, 2015, WIPO, 6 pages.

* cited by examiner

*Primary Examiner* — Michael Barker
*Assistant Examiner* — Amanda L Aguirre
(74) *Attorney, Agent, or Firm* — McCoy Russell LLP

(57) ABSTRACT

The present invention relates to a pharmaceutical composition and a cosmetic composition, which contain, as an active ingredient, a novel pseudo compound having similar structural characteristics to natural ceramide 1, or a pharmaceutically acceptable salt or solvate thereof, and the composition containing the compound of the present invention as an active ingredient has an excellent effect of enhancing a skin barrier function, thereby exhibiting an effect of alleviating inflammatory skin diseases, and has an excellent skin barrier improving function and an excellent skin moisturization enhancing effect.

10 Claims, 1 Drawing Sheet

PSEUDO CERAMIDE COMPOUND, AND PHARMACEUTICAL COMPOSITION AND COSMETIC COMPOSITION COMPRISING SAME

CROSS REFERENCE TO RELATED APPLICATIONS

The present application is a U.S. National Phase of International Patent Application Serial No. PCT/KR2014/012726, entitled "NOVEL PSEUDO CERAMIDE COMPOUND, AND PHARMACEUTICAL COMPOSITION AND COSMETIC COMPOSITION COMPRISING SAME," filed on Dec. 23, 2014, which claims priority to Korean Patent Application No. 10-2014-0004029, entitled "NOVEL PSEUDO CERAMIDE COMPOUND, AND PHARMACEUTICAL COMPOSITION AND COSMETIC COMPOSITION COMPRISING SAME," filed on Jan. 13, 2014, the entire contents of each of which are hereby incorporated by reference for all purposes.

TECHNICAL FIELD

The present invention relates to a novel pseudo ceramide compound having similar structural characteristics to natural ceramide, and a use thereof, and more specifically, to a novel pseudo ceramide compound having similar structural characteristics to natural ceramide 1, and a pharmaceutical composition and a cosmetic composition thereof.

BACKGROUND ART

Stratum corneum (SC) layer is the most important structure of a skin barrier function and is composed of corneocytes and stratum corneum (SC) intercellular lipid. A multilayer structure of SC intercellular lipid serves to prevent excessive loss of moisture and to suppress penetration of external allergen or hazardous materials into skin. Various kinds of lipids such as sphingolipids, phospholipids, cholesterol sulfate, neutral lipids, etc., are present among corneocytes of the stratum corneum layer. These lipids are present among the corneocytes to function as a skin barrier that prevents moisture evaporation in skin and protects skin from external stimulation or pollution. Ceramide, one of the lipid present in skin, is an N-acylated sphingoid compound, and is a signal transmitter which is involved in cell death. Ceramide synthesis in cells is performed by a complicated biosynthetic pathway of two molecules of serin and palmitoyl-CoA. It has been reported that a total of 11 kinds of ceramides is present in the human stratum corneum layer until now, and in particular, that ceramide 1 plays the most important role in a skin barrier function. Upon observing a structure of the human SC ceramide, a long chain fatty acid having C16 or more is a basic structure. Particularly, the ceramide 1 which is present in the largest content is formed by a combination of omega-hydroxy fatty acid and unsaturated fatty acid. Therefore, in order to synthesize functional pseudo ceramide, it is essential to smoothly supply long chain omega-hydroxy fatty acid.

Natural ceramides that are currently used are extracted mainly from nerve tissues (brain, spinal cord, etc.) of animals, and it is not possible to use the natural ceramides as raw materials for cosmetics due to concerns about safety of mad cow disease (BSE), etc. In addition, a synthetic ceramide is a ceramide produced through a fermentation process using a yeast and a synthesis process, and commercialized synthetic ceramides include ceramide III and ceramide IV. The synthetic ceramides have limitation in being used as a material for cosmetics due to high price of 1.5 to 2 million/kg.

In addition, the ceramide III and the ceramide IV have functional limitations in forming skin barrier and have significantly low solubility to cause problems such as precipitation in formulation, etc., such that it is difficult to use the ceramide III and the ceramide IV at a high concentration.

As compared to general moisturizers, it has been reported that a physiologic lipid mixture including ceramide-based raw materials promotes recovery of a damaged skin barrier function, and in particular, clinical trial results have been published that the physiologic lipid mixture exhibits similar effects to over-average steroids for external use in terms of improving symptoms of atopic dermatitis patients. Despite these advantages, the pseudo ceramide has a disadvantage in that it is difficult to be introduced into various formulations due to high price and low solubility.

In addition, as research has recently focused on a skin barrier function, moisturizers for improving skin barrier using ceramide or pseudo ceramide have been actively developed. Most of the pseudo ceramides that have been developed until now basically have a structure of ceramide III (Korean Patent Publication No. 10-0570553).

Accordingly, the present inventors synthesized a novel pseudo ceramide compound having similar structural characteristics to natural ceramide 1 by using a long chain omega-hydroxy fatty acid, and found that the novel pseudo ceramide compound provides an effect of promoting differentiation of keratinocyte as well as an effect of improving a skin barrier function by using the novel pseudo ceramide compound, and filed the present invention.

DISCLOSURE

Technical Problem

An object of the present invention is to provide a novel pseudo ceramide compound having similar structural characteristics to natural ceramide 1 exhibiting an excellent effect of improving a skin barrier function, a pharmaceutically acceptable salt or solvate thereof.

Another object of the present invention is to provide a pharmaceutical composition having an effect of improving a skin barrier function and an effect of alleviating inflammatory skin diseases, the pharmaceutical composition including: as an active ingredient, a novel pseudo ceramide compound, a pharmaceutically acceptable salt or solvate thereof.

Still another object of the present invention is to provide a cosmetic composition having a function of improving a skin barrier function and an effect of enhancing skin moisturization, the cosmetic composition including: as an active ingredient, a novel pseudo ceramide compound, a pharmaceutically acceptable salt or solvate thereof.

Technical Solution

In one general aspect, there is provided a pseudo ceramide compound represented by Chemical Formula 1 below, a pharmaceutically acceptable salt or solvate thereof:

[Chemical Formula 1]

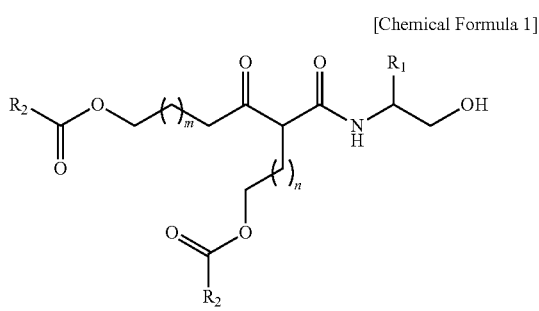

in Chemical Formula 1, $R_1$ is hydrogen or (C1-C10) hydroxyalkyl, $R_2$ is each independently (C4-C20) linear or branched alkyl, and m and n are each independently an integer of 1 to 18.

In the pseudo ceramide compound represented by Chemical Formula 1 according to an exemplary embodiment of the present invention, $R_1$ may be hydrogen or (C1-C4) hydroxyalkyl, and $R_2$ may be each independently (C5-C17) linear or branched alkyl.

In the pseudo ceramide compound represented by Chemical Formula 1 according to an exemplary embodiment of the present invention, m and n may be each independently an integer of 5 to 15.

The pseudo ceramide compound according to an exemplary embodiment of the present invention may be represented by the following structures:

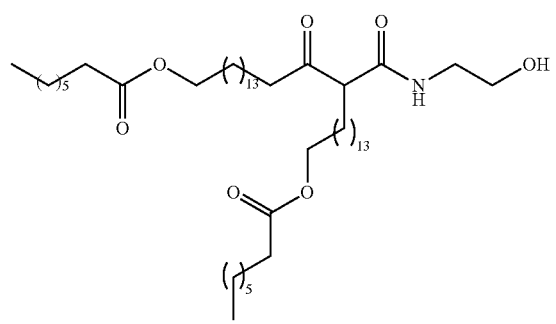

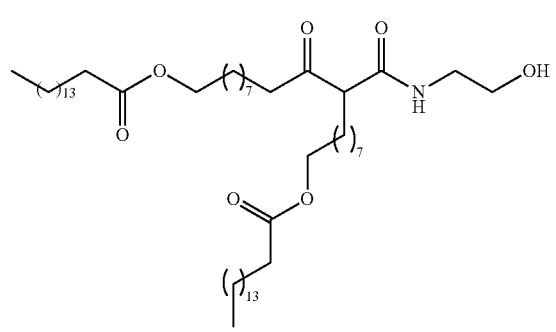

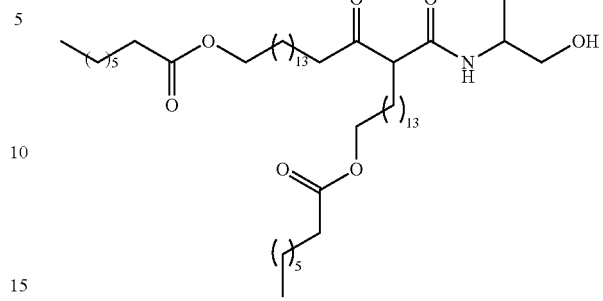

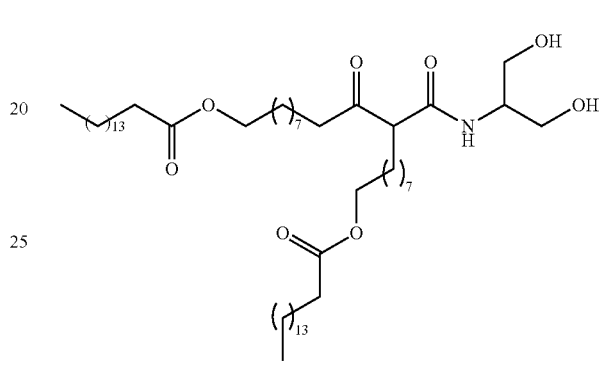

In another general aspect, there is provided a pharmaceutical composition having an effect of improving a skin barrier function and an effect of alleviating inflammatory skin diseases, the pharmaceutical composition including: as an active ingredient, the pseudo ceramide compound represented by Chemical Formula 1 above, a pharmaceutically acceptable salt or solvate thereof.

The inflammatory skin disease according to an exemplary embodiment of the present invention may be atopic dermatitis, allergic rhinitis, psoriasis, contact dermatitis, eczematous dermatitis, actinic dermatitis, seborrheic dermatitis, dermatitis herpetiformis, lichen planus, lichen sclerosis, necrotic pyoderma, pemphigus, bullous epidermal bullosa, vascular edema, blepharitis, allergic conjunctivitis, degenerative or inflammatory ophthalmitis, arthritis, rheumatoid arthritis, spondylitis, systemic sclerosis, dermatomyositis, polymyositis, inflammatory muscle disease, AIDS, leprosy, three digits syndrome, inflammatory bowel disease or stress disease.

The pharmaceutical composition according to an exemplary embodiment of the present invention may contain the pseudo ceramide compound, the pharmaceutically acceptable salt or solvate thereof in a content of 0.005 to 20 wt % based on total weight of the composition.

In still another general aspect, there is provided a cosmetic composition having a function of improving skin barrier and an effect of enhancing skin moisturization, the cosmetic composition including: as an active ingredient, the pseudo ceramide compound represented by Chemical Formula 1 above, a pharmaceutically acceptable salt or solvate thereof.

The cosmetic composition according to an exemplary embodiment of the present invention may have a formulation of skin lotion, skin softening lotion, skin toner, astringent, lotion, milk lotion, moisturizing lotion, nutrition lotion, massage cream, nourishing cream, moisturizing cream, hand cream, foundation, essence, nutrition essence, pack, soap, cleansing foam, cleansing lotion, cleansing cream, body lotion or body cleanser.

The cosmetic composition according to an exemplary embodiment of the present invention may contain the pseudo ceramide compound, the pharmaceutically acceptable salt or solvate thereof in a content of 0.005 to 20 wt % based on total weight of the composition.

Advantageous Effects

The present invention provides a novel pseudo ceramide compound represented by Chemical Formula 1 and having similar structural characteristics to natural ceramide 1, wherein the compound represented by Chemical Formula 1 according to the present invention, a pharmaceutically acceptable salt or solvate thereof has an effect of improving a skin barrier function to be capable of treating and preventing inflammatory skin diseases, which is useful as a cosmetic composition or a pharmaceutical composition.

BEST MODE

Figure 1:
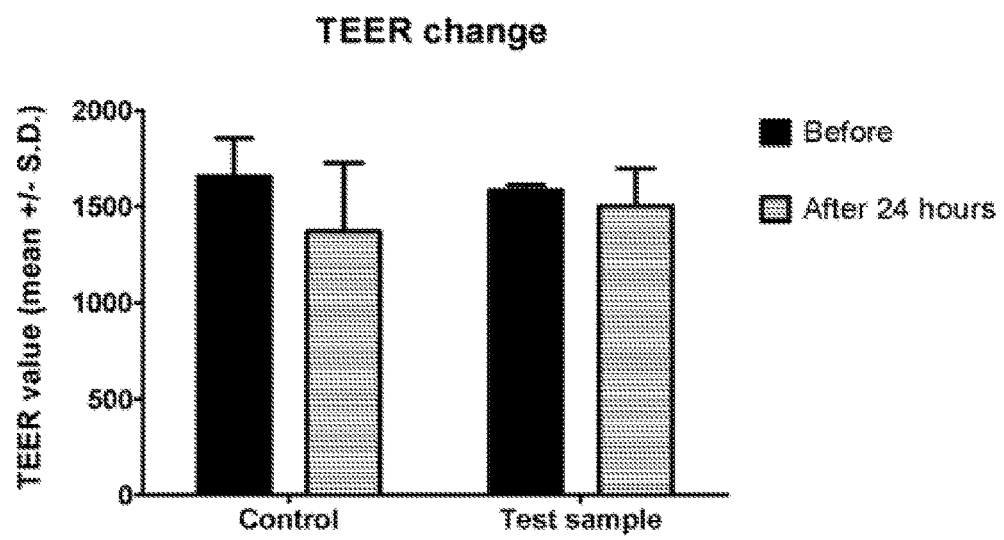
FIG. 1 illustrates TEER (transepithelial electrical resistance) results obtained by evaluating artificial skin integrity according to an exemplary embodiment of the present invention.

Hereinafter, a pseudo ceramide compound according to the present invention and a use thereof are described in detail. Here, unless technical and scientific terms used herein are defined otherwise, they have meanings generally understood by a person skilled in the art to which the present invention pertains. Known functions and configurations that may obscure the gist of the present invention with unnecessary detail will be omitted.

Terms used in the present specification are described as below.

"Evaluation of artificial skin integrity" refers to a method of measuring electrical resistance of artificial skin to evaluate a degree of improvement of a skin barrier function.

In addition, a "pharmaceutically acceptable salt" refers to a salt or a complex that retains desired biological activity of the pseudo ceramide compound according to the present invention, but exhibits undesirable toxic effects to a minimum or does not exhibit the undesirable toxic effects at all.

The present invention provides a pseudo ceramide compound represented by Chemical Formula 1 below, a pharmaceutically acceptable salt or solvate thereof:

[Chemical Formula 1]

in Chemical Formula 1, $R_1$ is hydrogen or (C1-C10) hydroxyalkyl, $R_2$ is each independently (C4-C20) linear or branched alkyl, and m and n are each independently an integer of 1 to 18.

In addition, it is preferred that the pseudo ceramide compound represented by Chemical Formula 1 according to the present invention may be a pseudo ceramide compound in which $R_1$ is hydrogen or (C1-C4) hydroxyalkyl, and $R_2$ is each independently (C5-C17) linear or branched alkyl, in order to form a stable lamellar layer, etc., but $R_1$ and $R_2$ of the present invention are not limited thereto. Here, it is more preferred that m and n may be an integer of 5 to 15 in order that an interlayer distance of the lamellar layer in the formulation is maintained to be 10 nm or more which is similar to the stratum corneum, but m and n of the present invention are not limited thereto.

The pseudo ceramide derivative, the pharmaceutically acceptable salt or solvate thereof according to the present invention may be selected from pseudo ceramide compounds represented by the following structures, but the present invention is not limited thereto:

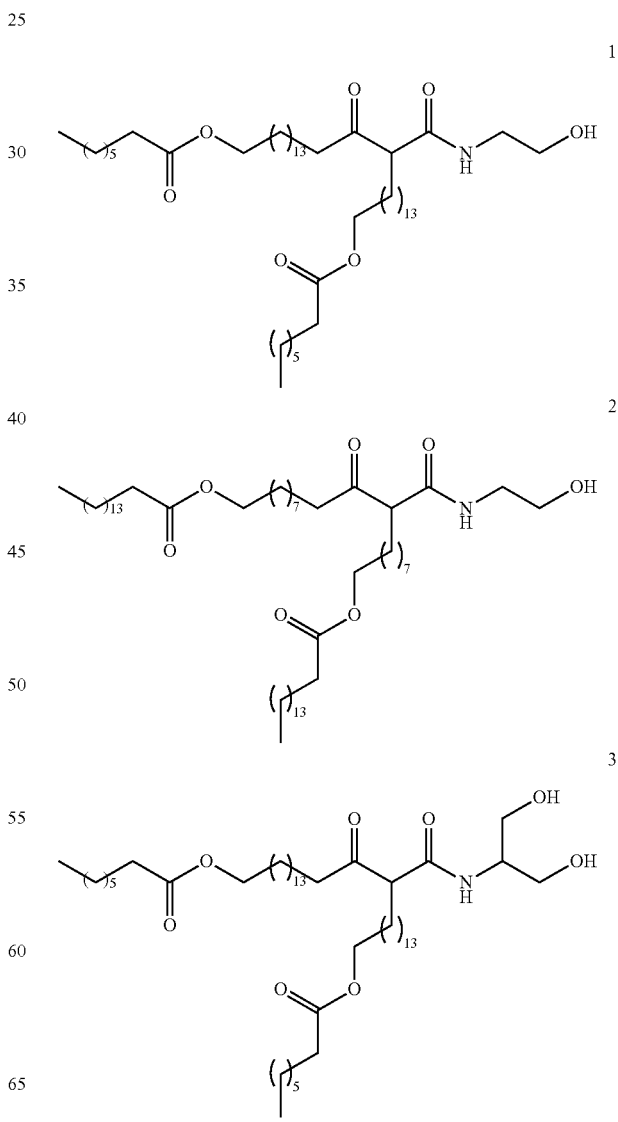

-continued

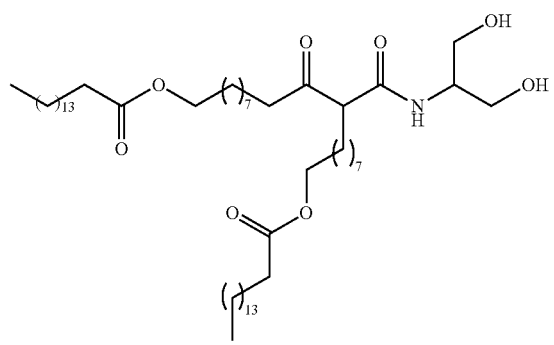

The pseudo ceramide compound represented by Chemical Formula 1 according to the present invention is not specifically limited, but may be prepared through organic reactions that are previously known through a route of Reaction Scheme 1 below:

[Reaction Scheme 1]

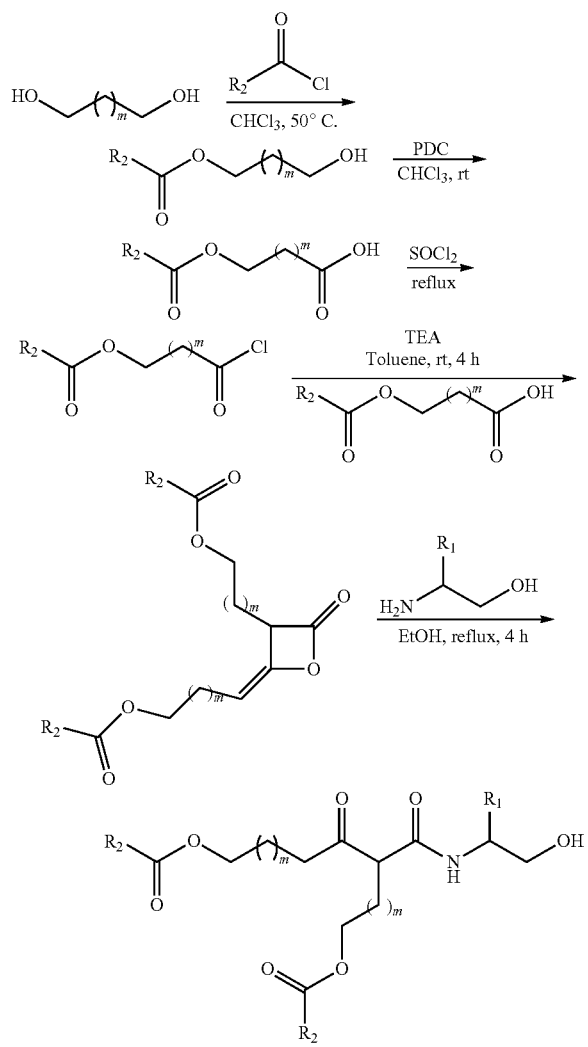

In addition, the present invention provides a pharmaceutical composition having an effect of improving a skin barrier function and an effect of alleviating inflammatory skin diseases, the pharmaceutical composition including: as an active ingredient, the pseudo ceramide compound according to the present invention, the pharmaceutically acceptable salt or solvate thereof.

The "pharmaceutically acceptable salt" according to the present invention may have a therapeutically active and non-toxic base or acid addition salt form that is capable of being formed by the pseudo ceramide compound represented by Chemical Formula 1.

Here, examples of the non-toxic base include sulfate, pyrosulfate, bisulfate, sulfite, bisulfite, nitrate, phosphate, mono-hydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propioleate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, β-hydroxybutyrate, glycolate, maleate, tartrate, methane sulfonate, propane sulfonate, naphthalene-1-sulfonate, naphthalene-2-sulfonate or mandelate, but the present invention is not limited thereto.

In addition, the acid addition salt may be an acid addition salt formed by pharmaceutically acceptable free acid. Preferably, the acid addition salt may be an inorganic acid such as hydrochloric acid, nitric acid, phosphoric acid, sulfuric acid, hydrobromic acid, hydroiodic acid, nitrous acid, or phosphorous acid, an aromatic acid such as aliphatic mono- or dicarboxylate, phenyl-substituted alkanoate, hydroxy alkanoate or alkanedioate, or aliphatic or aromatic sulfonic acid, or an organic acid such as acetic acid, benzoic acid, citric acid, lactic acid, maleic acid, gluconic acid, methanesulfonic acid, 4-toluenesulfonic acid, tartaric acid, or fumaric acid, but the examples of the acid addition salt are not limited thereto.

A solvent of the solvate is not specifically limited, but may be preferably a hydrate or an alcoholic material.

In addition, it is intended that the compound of the present invention includes respective possible isomeric forms and mixtures thereof unless a specific isomer is stated specifically.

The compound according to the present invention may be present in various polymorphic forms. Although the various polymorphic forms are not explicitly shown in the above Formula, it is intended that these forms are included within the scope of the present invention.

The inflammatory skin disease may be atopic dermatitis, allergic rhinitis, psoriasis, contact dermatitis, eczematous dermatitis, actinic dermatitis, seborrheic dermatitis, dermatitis herpetiformis, lichen planus, lichen sclerosis, necrotic pyoderma, pemphigus, bullous epidermal bullosa, vascular edema, blepharitis, allergic conjunctivitis, degenerative or inflammatory ophthalmitis, arthritis, rheumatoid arthritis, spondylitis, systemic sclerosis, dermatomyositis, polymyositis, inflammatory muscle disease, AIDS, leprosy, three digits syndrome, inflammatory bowel disease or stress disease.

The present invention may include at least one compound of the present invention in a pharmaceutically acceptable carrier.

Further, the pharmaceutical composition of the present invention may include a pharmaceutically acceptable carrier according to methods that are capable of being easily practiced by a person skilled in the art. The pharmaceutically acceptable carrier contained in the pharmaceutical composition of the present invention, which is generally used in preparation, may be lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, or mineral oil, but the present invention is not limited thereto. The pharmaceutical composition of the present invention may further contain a lubricant, a wetting agent, a sweetening agent, an odorant, an emulsifier, a suspension, a preservative, and the like, in addition to the above ingredients.

The pharmaceutical composition of the present invention may be prepared as general formulations by using the pharmaceutically acceptable carriers and/or excipients according to methods capable of being easily practiced by a person skilled in the art, to be prepared as a unit dosage form or to be prepared by introducing the composition into a multi-dosage container. The general formulation refers to oral (including tablets, capsules, and powders), intrabuccal, sublingual, intrarectal, intravaginal, intranasal, topical or parenteral (including intravenous, cavernous, intramuscular, subcutaneous, and intravascular injections) administration formulation. For example, the compound according to the present invention may be parenterally, intrabuccally or sublingually administered as a table form containing starch or lactose, or a capsule form containing the compound alone or excipient, or a suspension form containing chemicals to provide flavor or exhibit color. Liquid formulation is a semisynthetic glyceride such as suspension, for example, methyl cellulose, witepsol, or a mixture of apricot kernel oil and PEG-6 ester, or a glyceride mixture such as a mixture of PEG-8 and caprylic/capric glyceride, and may be prepared together with pharmaceutically acceptable additives. In addition, in the case where the compound is administered through parenteral injections such as intravenous, cavernous, intramuscular, subcutaneous, and intravascular injections, an aseptic aqueous solution form is the most preferred, wherein the solution may also contain other materials (for example, salt, monosaccharide such as mannitol or glucose) in order to have isotonicity with blood.

Specifically, the pharmaceutical composition according to an exemplary embodiment of the present invention may be used in a form of tablet, pill, capsule, granule, powder, solution, patch, transdermal patch using microneedle or injection.

The compound of the present invention may be included in the pharmaceutical composition in a content sufficient to obtain desirable effects depending on processes or disease states.

The pharmaceutical composition may contain the pseudo ceramide compound, the pharmaceutically acceptable salt or solvate thereof in a content of 0.005 to 20 wt %, preferably, 0.1 to 10 wt %, based on total weight of the composition, but the content thereof is not limited thereto. Here, when the content of the pseudo ceramide compound, the pharmaceutically acceptable salt or solvate thereof is less than 0.005 wt %, the effect may not be significant. When the content of the pseudo ceramide compound, the pharmaceutically acceptable salt or solvate thereof is more than 20 wt %, it is not preferred since stability may be deteriorated and solubility in the formulation may be deteriorated.

In addition, there is provided a cosmetic composition having a function of improving a skin barrier and an effect of enhancing skin moisturization, the cosmetic composition including: as an active ingredient, the pseudo ceramide compound represented by Chemical Formula 1 above, a pharmaceutically acceptable salt or solvate thereof.

The cosmetic composition is not specifically limited, but preferably, may have a formulation of skin lotion, skin softening lotion, skin toner, astringent, lotion, milk lotion, moisturizing lotion, nutrition lotion, massage cream, nourishing cream, moisturizing cream, hand cream, foundation, essence, nutrition essence, pack, soap, cleansing foam, cleansing lotion, cleansing cream, body lotion or body cleanser. In addition, the compound of the present invention may have excellent solubility to be easily usable in the cosmetic composition. The cosmetic composition may contain the compound as an active ingredient to be usable for a function of improving skin barrier and for skin moisturization.

The formulation of the cosmetic composition is not specifically limited, but may be preferably, solutions, emulsions, pastes, creams, gels or surfactant-containing cleansing products. Here, when the formulation of the composition is a solution or an emulsion, solvents, a solubilizer, or an emulsifying agent is used as a carrier component. For example, preferably, water, ethanol, isopropanol, ethyl carbonate, ethyl acetate, benzyl alcohol, benzyl benzoate, propylene glycol, 1,3-butyl glycol oil, glycerol aliphatic ester, fatty acid ester of polyethylene glycol or sorbitan may be included as the carrier component, but examples thereof are not limited thereto. In addition, when the formulation of the composition is a cream or a gel, animal fibers, plant fibers, waxes, paraffins, starch, tragacanth, cellulose derivatives, polyethylene glycol, silicon, bentonite, silica, talc or zinc oxide may be used as the carrier component. When the formulation of the composition is a surfactant-containing cleansing, aliphatic alcohol sulfate, aliphatic alcohol ether sulfate, sulfosuccinate monoester, isethionate, imidazolinium derivative, methyl taurate, sarcosinate, fatty acid amide ether sulfate, alkyl amido betaine, aliphatic alcohol, fatty acid glyceride, fatty acid diethanolamide, vegetable oil, lanolin derivative or ethoxylated glycerol fatty acid ester may be used as the carrier component.

The cosmetic composition may contain the pseudo ceramide compound, the pharmaceutically acceptable salt or solvate thereof in a content of 0.005 to 20 wt %, preferably, 0.1 to 10 wt %, based on total weight of the composition, but the content thereof is not limited thereto. Here, when the content of the pseudo ceramide compound, the pharmaceutically acceptable salt or solvate thereof is less than 0.005 wt %, the effect may not be significant. When the content of the pseudo ceramide compound, the pharmaceutically acceptable salt or solvate thereof is more than 20 wt %, it is not preferred since stability may be deteriorated and solubility in the formulation may be deteriorated.

The cosmetic composition may further include functional additives or components included in general cosmetic compositions in addition to the pseudo ceramide compound, the pharmaceutically acceptable salt or solvate thereof. Here, the functional additive may include at least one selected from the group consisting of water-soluble vitamins, fat-soluble vitamins, peptide polymers, polysaccharide polymers, sphingolipids and seaweed extracts. The component included in general cosmetic compositions may be oil and fat components, moisturizers, emollients, surfactants, organic or inorganic pigments, organic powder, ultraviolet absorbents, antiseptics, disinfectants, antioxidants, plant extracts, pH adjusters, alcohol, pigments, perfumes, blood circulation promoters, cooling agents, adiaphoretics or purified water, and may be usable by being easily selected by a person skilled in the art.

Hereinafter, preferred Examples of the present invention will be described to assist in the understanding of the present invention. However, the following Examples are provided by way of example only so that a person skilled in the art can fully understand the disclosures of the present invention. Therefore, the scope of the present invention is not limited to these Examples.

[Example 1] Preparation of Pseudo Ceramide Compound 1

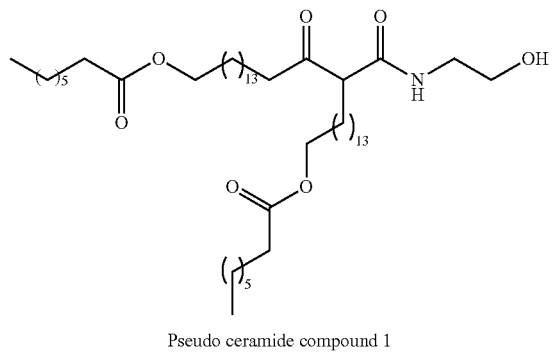

Pseudo ceramide compound 1

[Step 1] Preparation of 16-(octanoyloxy)hexadecanoic acid

16-Hydroxyhexadecanoic acid (2.0 g) (7.34 mmol) was dissolved in chloroform (60 ml) at 70° C., and octanoyl chloride (1.38 ml) (8.07 mmol) was added thereto. The mixture was stirred under reflux for 4 hours. A reaction temperature was lowered to room temperature, and purified water and dichloromethane were added to the mixture and stirred. The resultant mixture was stood, and an organic layer was separated and washed with brine once. The organic layer was dried over anhydrous magnesium sulfate ($MgSO_4$), and filtered. The filtrate was concentrated under reduced pressure. The residue was separated by column chromatography (dichloromethane:Methanol=50:1) to obtain a white solid compound (2.93 g, 7.34 mmol, 100% yield).

[Step 2] Preparation of 16-(octanoyloxy)hexadecanoylketenedimer 16-(octanoyloxy)hexadecanoic acid (2.0 g) (5.02 mmol) was dissolved in thionyl chloride (1.83 ml) (25.1 mmol) under nitrogen atmosphere and stirred under reflux for 2 hours. 15-(chlorocarbonyl) pentadecyl octanoate prepared by removing thionyl chloride under vacuum was dissolved in toluene (12 ml) under nitrogen atmosphere, and a reactor temperature was cooled to be 0° C. or less by using an ice bath and triethylamine (TEA) (1.4 ml) (10.04 mmol) was slowly added thereto. After the addition was completed, the ice bath was removed, and the reactor temperature was slowly raised to room temperature, and the mixture was stirred for 4 hours. Purified water was added to the reaction mixture, and hydrochloric acid was added thereto so as to control the pH to be 3. Further, purified water and ethyl acetate were added thereto and stirred, and the reaction mixture was stood, and an organic layer was separated. The organic layer was washed with brine once, and dried over anhydrous magnesium sulfate ($MgSO_4$). The resultant material was filtered, and the filtrate was concentrated under reduced pressure. The residue was separated by column chromatography (ethyl acetate:hexane=1:30) to obtain 16-(octanoyloxy)hexadecanoylketenedimer as a light yellow solid (270 mg, 0.35 mmol, 14% yield).

[Step 3] Preparation of Pseudo Ceramide Compound 1

16-(octanoyloxy)hexadecanoylketenedimer (270 mg) (0.35 mmol) was dissolved in ethanol (2.7 ml), and ethanolamine (0.043 ml) (0.71 mmol) was added to this solution and stirred for 4 hours at 60° C. The reaction was confirmed by TLC, and the solvent was removed by concentration under reduced pressure. Ethyl acetate and purified water were added to the concentrated material, and hydrochloric acid was added thereto so as to control the pH to be 3. Further, the resultant mixture was stirred, and stood, and an organic layer was separated. The organic layer was dried over anhydrous magnesium sulfate ($MgSO_4$) and filtered, and the filtrate was concentrated under reduced pressure. A solvent thereof was completely removed, and residue was separated by column chromatography (dichloromethane:methanol=40:1) to obtain a light yellow solid compound (186 mg, 0.23 mmol, 66% yield).

$^1$H-NMR (600 MHz, chloroform-d1): 6.74 (s, 1H), 4.05 (t, J=7.2 Hz, 4H), 3.71 (t, J=5.4 Hz, 2H), 3.43-3.39 (m, 3H), 2.58-2.52 (m, 3H), 2.29 (t, J=7.8 Hz, 4H), 1.84-1.80 (m, 2H), 1.62-1.55 (m, 10H), 1.31-1.25 (m, 60H), 0.88 (t, J=7.2 Hz, 6H).

MS (ESI pos. ion) m/z: 822 (M+). Calc'd exact mass for C50H95NO7: 822.29.

[Example 2] Preparation of Pseudo Ceramide Compound 2

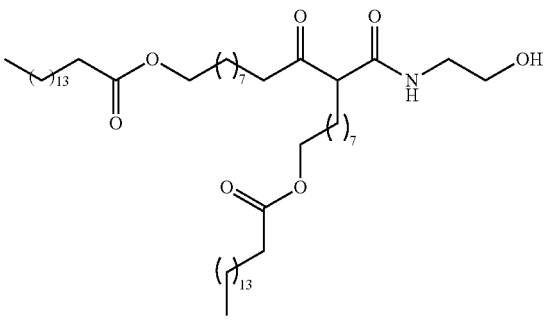

Pseudo ceramide compound 2

[Step 1] Preparation of 10-hydroxydecyl palmitate 1,10-decandiol (20.0 g) (114.76 mmol) was dissolved in chloroform (600 ml) at 65° C., and palmitoyl chloride (17.5 ml) (57.38 mmol) was slowly added thereto. The mixture was stirred under reflux for 12 hours, and concentrated until an amount of solvent of the reaction mixture was about 300 ml. 1,10-Decandiol remaining after the reaction was removed by filtration, and the filtrate thereof was completely concentrated, and the residue was separated by column chromatography (dichloromethane:methanol=50:1) to obtain a white solid compound (20.9 g, 50.64 mmol, 88% yield).

[Step 2] Preparation of 10-(palmitoyloxy)decanoic acid

Pyridinium dichromate (32.7 g) (151.9 mmol) was added to chloroform (629 ml), and a solution in which 10-hydroxydecyl palmitate (20.9 g) (50.6 mmol) is dissolved in chloroform (209 ml) was slowly added to the resultant suspension, followed by stirring at room temperature for 24 hours. Purified water was added to the reaction mixture, and stirred, and the resultant mixture was stood. An organic layer was separated, dried over anhydrous magnesium sulfate ($MgSO_4$), and filtered. The filtrate was concentrated under reduced pressure. The residue was separated by column chromatography (dichloromethane:Methanol=40:1) to obtain a white solid compound (10.0 g, 23.4 mmol, 46% yield).

[Steps 3 to 4] Preparation of 10-(palmitoyloxy)decanoyl ketenedimer 10-(palmitoyloxy)decanoic acid (5.0 g) (11.7 mmol) was dissolved in thionyl chloride (4.3 ml) (58.6 mmol) under nitrogen atmosphere and stirred under reflux for 2 hours. 9-(chlorocarbonyl)nonyl palmitate prepared by removing thionyl chloride under vacuum was dissolved in toluene (30 ml) under nitrogen atmosphere, and a reactor temperature was cooled to be 0° C. or less by using an ice bath and TEA (3.3 ml) (23.4 mmol) was slowly added thereto. After the addition was completed, the ice bath was removed, and the reactor temperature was slowly raised to room temperature, and the mixture was stirred overnight. Purified water was added to the reaction mixture, and hydrochloric acid was added thereto so as to control the pH to be 3. Further, purified water and ethyl acetate were added thereto and stirred, and the reaction mixture was stood, and an organic layer was separated. The organic layer was washed with brine once. The organic layer was dried over anhydrous magnesium sulfate ($MgSO_4$), and filtered. The filtrate was concentrated under reduced pressure. The residue was separated by column chromatography (ethyl acetate:hexane=1:10) to obtain 10-(palmitoyloxy)decanoyl ketenedimer as a light yellow solid (1.47 g, 0.35 mmol, 30.8% yield).

[Step 5] Preparation of Pseudo Ceramide Compound 2

10-(palmitoyloxy)decanoyl ketenedimer (1.34 g) (1.64 mmol) was dissolved in ethanol (13 ml), and ethanolamine (0.2 ml) (3.28 mmol) was added to this solution and stirred at 40° C. overnight. The reaction was confirmed by TLC, and the solvent was removed by concentration under reduced pressure. Ethyl acetate and purified water were added to the concentrated material, and hydrochloric acid was added thereto so as to control the pH to be 3. Further, the resultant mixture was stirred, and stood, and an organic layer was separated. The organic layer was dried over anhydrous magnesium sulfate ($MgSO_4$) and filtered, and the filtrate was concentrated under reduced pressure to completely remove the solvent. The residue was separated by column chromatography (dichloromethane:Methanol=40:1) to obtain a light yellow solid compound (810 mg, 0.92 mmol, 56% yield).

$^1$H-NMR (600 MHz, chloroform-d1): 6.69 (br s, 1H), 4.05 (m, 4H), 3.71 (t, J=5.4 Hz, 2H), 3.44-3.38 (m, 3H), 2.56-2.49 (m, 3H), 2.29 (t, J=7.2 Hz, 4H), 1.82-1.80 (m, 2H), 1.62-1.54 (m, 10H), 1.29-1.21 (m, 68H), 0.88 (t, J=7.2 Hz, 6H).

MS (ESI pos. ion) m/z: 878 (M+). Calc'd exact mass for C54H103NO7: 878.40.

[Preparation Example 1] Preparation of Cosmetic Composition

Cosmetic compositions (Test formulation and control formulation) were prepared according to compositions of Table 1 below.

TABLE 1

| Raw Material | Test Formulation | Control Formulation |
|---|---|---|
| Myristoyl/Palmitoyl oxostearamide/Arachamide MEA | 1 | 1 |
| Sorbitan stearate | 5 | 5 |
| Stearic acid | 4.5 | 4.5 |
| Cetearyl alcohol | 10.5 | 10.5 |
| Carbomer | 0.1 | 0.1 |
| Example 1 | 0.1 | — |
| Caprylic/Capric triglyceride | 15 | 15 |
| Glycerin | 10 | 10 |
| Purified water | Residual content | Residual content |
| Sum | 100 | 100 |

[Test Example 1] Evaluation of Artificial Skin Integrity

A test formulation containing myristoyl/palmitoyl oxostearamide/arachamide MEA (Product name: PC-9S) which is a pseudo ceramide and Example 1 in a predetermined amount (about 500 mg) was applied to artificial skin (Keraskin™ from MCTT, Seoul, Korea). Then, skin integrity before the application and after 24 hours of the application was evaluated through TEER (trans-epithelial electrical resistance) measurement.

For the control formulation, skin integrity of the control formulation was evaluated through TEER (trans-epithelial electrical resistance) measurement in the same method as above except that the control formulation did not contain Example 1. Respective results were illustrated in FIG. 1.

As a result, it could be confirmed that the test formulation containing Example 1 had an effect of maintaining 12.3% or more of skin integrity as compared to the control formulation.

[Test Example 2] Measurement of Effect of Promoting Differentiation of Artificial Skin A test formulation containing myristoyl/palmitoyl oxostearamide/arachamide MEA (Product name: PC-9S) which is a pseudo ceramide and Example 1 in a predetermined amount (about 500 mg) was applied to artificial skin (Keraskin™ from MCTT, Seoul, Korea). Then, after 24 hours, expression aspects of filaggrin which is a differentiation indicator protein were observed by immunohistochemical stain.

Figure 2:
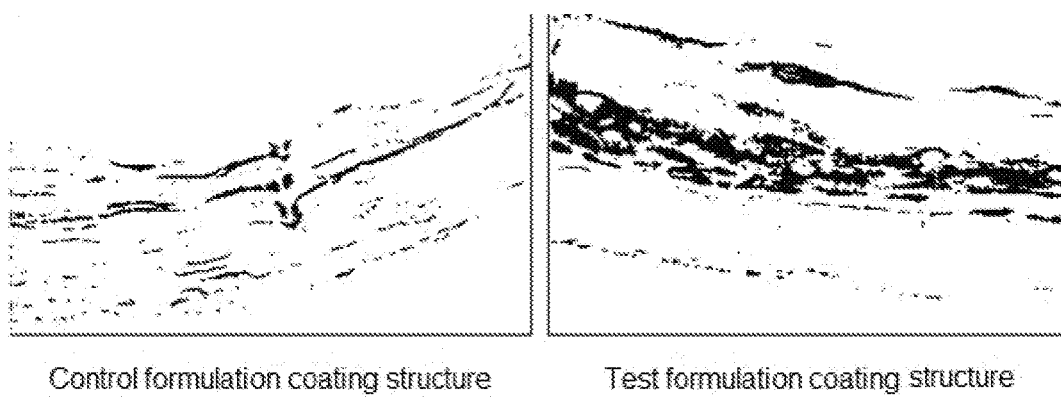
FIG. 2 illustrates results of expression aspects of filaggrin which is a differentiation indicator protein observed by an immunohistochemical stain in order to measure an effect of promoting differentiation of artificial skin according to an exemplary embodiment of the present invention.

For the control formulation, expression aspects of filaggrin which is a differentiation indicator protein were observed by immunohistochemical stain in the same method as above except that the control formulation did not contain Example 1. Respective results were illustrated in FIG. 2.

As a result, it could be confirmed that the test formulation containing Example 1 exhibited remarkably increased expression of the differentiation indicator protein (filaggrin) in the artificial skin as compared to the control formulation, such that the test formulation containing Example 1 had an effect of skin differentiation.

The invention claimed is:

1. A pseudo ceramide compound represented by Chemical Formula 1 or a pharmaceutically acceptable salt or a solvate thereof:

[Chemical Formula 1]

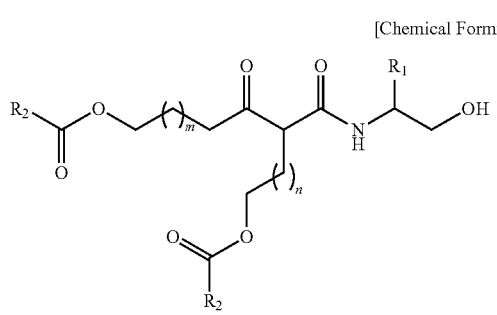

in Chemical Formula 1, $R_1$ is hydrogen or (C1-C10) hydroxyalkyl, $R_2$ is each independently (C4-C20) linear or branched alkyl, and m and n are each independently an integer of 1 to 18.

2. The pseudo ceramide compound, or the pharmaceutically acceptable salt or the solvate thereof of claim 1, wherein $R_1$ is hydrogen or (C1-C4) hydroxyalkyl, and $R_2$ is each independently (C5-C17) linear or branched alkyl.

3. The pseudo ceramide compound, or the pharmaceutically acceptable salt or the solvate thereof of claim 2, wherein m and n are each independently an integer of 5 to 15.

4. The pseudo ceramide compound, or the pharmaceutically acceptable salt or the solvate thereof of claim 2, wherein it is represented by one of the following structures:

1

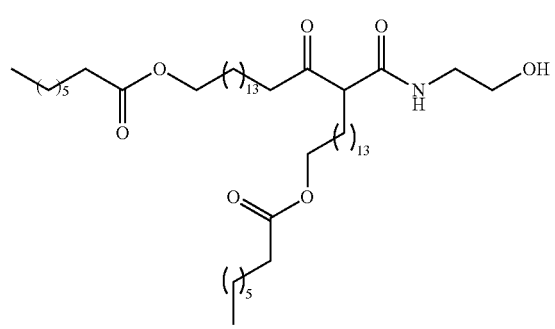

2

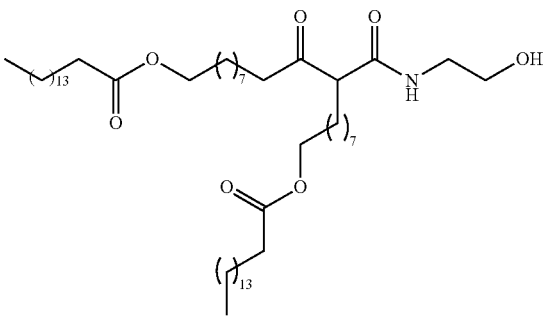

3

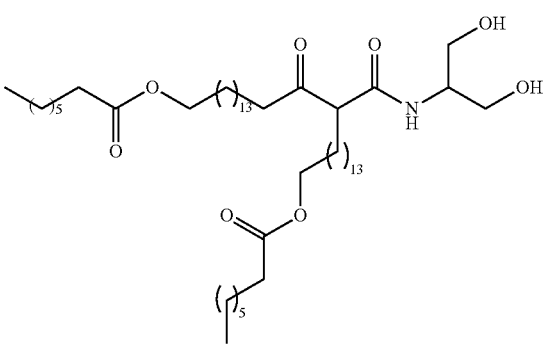

4

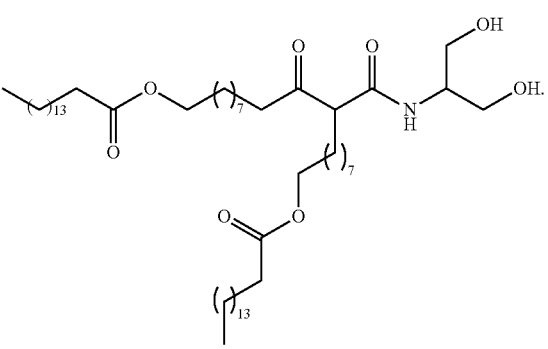

5. A pharmaceutical composition having an effect of improving a skin barrier function comprising: as an active ingredient, a pseudo ceramide compound represented by Chemical Formula 1 or a pharmaceutically acceptable salt or a solvate thereof:

[Chemical Formula 1]

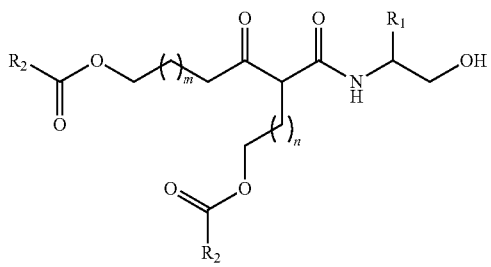

in Chemical Formula 1, $R_1$ is hydrogen or (C1-C10) hydroxyalkyl,

R₂ is each independently (C4-C20) linear or branched alkyl, and m and n are each independently an integer of 1 to 18.

6. The pharmaceutical composition of claim 5, wherein the pharmaceutical composition contains the pseudo ceramide compound represented by Chemical Formula 1 or the pharmaceutically acceptable salt or the solvate thereof in a content of 0.005 to 20 wt % based on total weight of the composition.

7. A cosmetic composition having a function of improving skin barrier and an effect of enhancing skin moisturization, the cosmetic composition comprising: as an active ingredient, a pseudo ceramide compound represented by Chemical Formula 1 or a pharmaceutically acceptable salt or a solvate thereof:

[Chemical Formula 1]

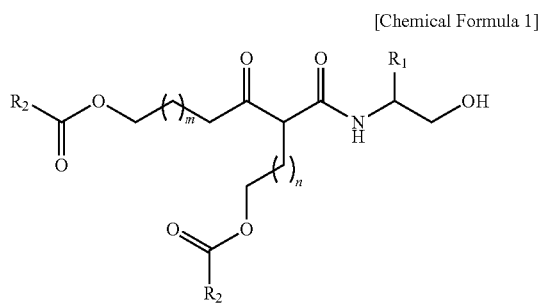

in Chemical Formula 1,

R₁ is hydrogen or (C1-C10) hydroxyalkyl,

R₂ is each independently (C4-C20) linear or branched alkyl, and m and n are each independently an integer of 1 to 18.

8. The cosmetic composition of claim 7, wherein the cosmetic composition has a formulation of skin lotion, skin softening lotion, skin toner, astringent, lotion, milk lotion, moisturizing lotion, nutrition lotion, massage cream, nourishing cream, moisturizing cream, hand cream, foundation, essence, nutrition essence, pack, soap, cleansing foam, cleansing lotion, cleansing cream, body lotion or body cleanser.

9. The cosmetic composition of claim 8, wherein the cosmetic composition contains the pseudo ceramide compound represented by Chemical Formula 1 or the pharmaceutically acceptable salt or the solvate thereof in a content of 0.005 to 20 wt % based on total weight of the composition.

10. A method for treating an inflammatory skin disease, comprising administering an effective amount of a pseudo ceramide compound represented by Chemical Formula 1 or a pharmaceutically acceptable salt or a solvate thereof to a subject in need thereof, wherein the skin disease is selected from the group consisting of atopic dermatitis, psoriasis, contact dermatitis, eczematous dermatitis, seborrheic dermatitis, dermatitis herpetiformis, lichen planus, lichen sclerosis, necrotic pyoderma, pemphigus, and bullous epidermal bullosa:

[Chemical Formula 1]

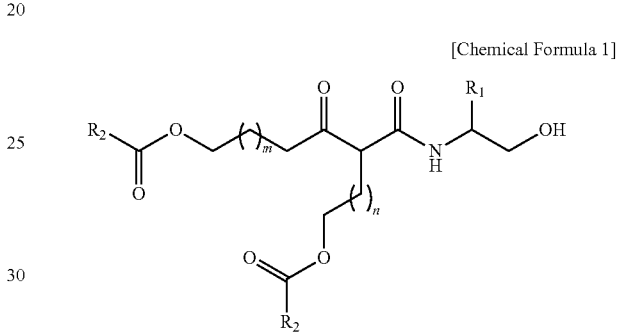

in Chemical Formula 1,

R₁ is hydrogen or (C1-C10) hydroxyalkyl,

R₂ is each independently (C4-C20) linear or branched alkyl, and m and n are each independently an integer of 1 to 18.

* * * * *